US005470737A

United States Patent [19]

Weinshilboum et al.

[11] Patent Number: 5,470,737

[45] Date of Patent: Nov. 28, 1995

[54] STABLY-TRANSFORMED CELLS EXPRESSING HUMAN THIOPURINE METHYLTRANSFERASE

[75] Inventors: Richard M. Weinshilboum, Rochester; Ronald Honchel, Kasson; Ibrahim A. Aksoy, Rochester; Carol L. Szumlanski, Rochester; Thomas C. Wood, Rochester; Diane M. Otterness, Rochester; Eric D. Wieben, Rochester, all of Minn.

[73] Assignee: Mayo Foundation for Medical Education and Research, Rochester, Minn.

[21] Appl. No.: 317,707

[22] Filed: Oct. 3, 1994

Related U.S. Application Data

[63] Continuation of Ser. No. 74,348, Jun. 9, 1993, abandoned.

[51] Int. Cl.$^6$ .............................. C12N 5/10; C12N 9/10; C07H 15/12

[52] U.S. Cl. .................................... 435/240.2; 435/172.3; 435/320.1; 435/193; 536/23.1; 536/23.5; 536/23.2

[58] Field of Search ........................ 536/23.1, 23.2–23.5; 435/240.21, 193, 172.3, 320.1, 240.2, 91.4, 91.2; 930/240; 935/9, 11, 14, 32, 40

[56] References Cited

U.S. PATENT DOCUMENTS

| | | | |
|---|---|---|---|
| 4,675,285 | 6/1985 | Clark et al. | 435/6 |
| 4,740,461 | 4/1988 | Kaufman | 435/69.1 |

OTHER PUBLICATIONS

Van Loon et al. 1990 FASEB J. 4(3): A755 Abstract 2836.

Woodson et al. 1983. Biochem. Pharmacol. 32(5): 819–826.

Honchel et al. (1993) FASEB. J., 7, A51, Abstract No. 294.

Wong et al. (1985) Science 228, 810–815.

Sambrook et al. 1989 in: Molecular Cloning, A Laboratory Manual. Second Edition, Cold Spring Harbor Laboratory Press, Cold Spring Harbor, N.Y. pp. 8.46, 8.47, 8.78, 8.79, 9.52, 9.53.

M. M. Ames et al., "Thiopurine Methyltransferase: Structure–Activity Relationships for Benzoic Acid Inhibitors and Thiophenol Substrates", *J. Med. Chem.*, 29, 354 (1986).

R. Chocair et al., "The Importance of Thiopurine Methyltransferase Activity for the Use of Azathioprine in Transplant Recipients", *Transplantation*, 53, 1051 (1992).

T. A. Glauser et al., "Human Hepatic Microsomal Thiol Methyltransferase", *Drug Metabolism and Diposition*, 20, 247 (1992).

T. Gomi et al., "Rat Guanidinoacetate Methyltransferase: Mutation of Amino Acids With a Common Sequence Motif of Mammalian Methyltransferase Does Not Affect Catalytic Activity but Alters Proteolytic Susceptibility", *Int. J. Biochem.*, 24, 1639 (1992).

D. Ingrosso et al., "Sequence of the D–Aspartyl/L–Isoaspartyl Protein Methyltransferase from Human Erythrocytes", *J. Biol. Chem.*, 264, 20131 (1989).

L. Lennerd, "Genetic Variation in Response to 6–Mercaptopurine for Childhood Acute Lymphoblastic Leukaemia", *Lancet*, 336–225 (1990).

Merrifield, "Solid Phase Peptide Synthesis. I. The synthesis of a Tetrapeptide", *J. Am. Chem. Soc.*, 85, 2149 (1963).

C. N. Remy et al., "Metabolism of Thiopyrimidines and Thiopurines", *J. Biol. Chem.*, 238, 1078 (1963).

C. L. Szumlanski et al., "Human Liver Thiopurine Methyltransferase Pharmacogenetics: Biochemical Properties, Liver–erythrocyte Correlation and Presence of Isozymes", *Pharmacogenetics*, 2, 148 (1992).

(List continued on next page.)

*Primary Examiner*—Christopher S. F. Low
*Attorney, Agent, or Firm*—Schwegman, Lundberg & Woessner

[57] ABSTRACT

A recombinant DNA sequence is provided which encodes human thiopurine methyl transferase (TPMT), as well as a mammalian cell line having said recombinant DNA sequence incorporated into the genome thereof, so that the cells express high levels of human TPMT activity.

9 Claims, 7 Drawing Sheets

OTHER PUBLICATIONS

A. Thithapandha et al., "Brain Histamine N–Methyl–Transferase Purification, Mechanism of Action, and Inhibition by Drugs", *Biochem. Pharmacol.*, 27, 263 (1978).

J. A. Van Loon et al., "Thiopurine Methyltransferase Isozymes in Human Renal Tissue", *Drug Met. Disposit.*, 18, 632 (1990).

R. M. Weinshilboum et al., "Calcium Inhibition of Rat Liver Catechol–O–Methyltransferase", *Biochem. Pharmacol.*, 25, 573 (1976).

R. M. Weinshilboum et al., "Human Erythrocyte Thiol Methyltransferase: Radiochemical Microassay and Biochemical Properties", *Clin. Chim. Acta*, 97, 59 (1979).

R. M. Weinshilboum et al., "Mercaptopurine Pharmacogenetics: Monogenic Inheritance of Erythrocyte Thiopurine Methyltransferase Activity", *Am. J. Human Genet.*, 32, 651 (1980).

R. M. Weinshilboum et al., "Tpmt and Ly–28: Localization on Mouse Chromosome 13", *Mouse Genome*, 90, 446 (1992).

L. C. Woodson et al., "Human Kidney Thiopurine Methyltransferase: Purification and Biochemical Properties", *Biochem. Pharmacol.*, 32, 819 (1983).

L. C. Woodson et al., "Thiopurine Methyltransferase: Aromatic Thiol Substrates and Inhibition by Benzoic Acid Derivatives", *Mol. Pharmacol.*, 24, 471 (1993).

G. Wu et al., "Isolation and characterization of *Escherichia coli* Mutants Affected in Aerobic Respiration: The Cloning and Nucleotide Sequence of ubiG",*J. Gen. Microbiol.*, 138, 2101 (1992).

HUMAN KIDNEY TPMT

| | PAPAIN 21 kDa | V8 18 kDa | CNBr 5 kDa | CNBr 19 kDa |
|---|---|---|---|---|
| 1 | V | | F | D |
| 2 | E | | S | G |
| 3 | I | | L | T |
| 4 | S | | L | R |
| 5 | E | | D/G | T |
| 6 | L | | K | S |
| 7 | G | | K | L |
| 8 | I | | F | D |
| 9 | Q | | S/Q | I |
| 10 | E | | Y | E |
| 11 | F-------- | F | L | E |
| 12 | F-------- | F | L | Y |
| 13 | T-------- | T | | |
| 14 | E-------- | E | | |
| 15 | Q-------- | Q | | |
| 16 | N-------- | N | | |
| 17 | L-------- | L | | |
| 18 | | S | | |
| 19 | | Y | | |
| 20 | | "X" | | |
| 21 | | E | | |
| 22 | | E | | |
| 23 | | P | | |
| 24 | | I | | |
| 25 | | T | | |

FIG. 1

TPMT cDNA: T84 HUMAN COLON CARCINOMA CELLS

```
CGGCAACCAGCTGTAAGCGAGGCACGGAAGACATATGCTTGTGAGACAAAGGTGTCTCTG   -6
     1
AAACTATGGATGGTACAAGAACTTCACTTGACATTGAAGAGTACTCGGATACTGAGGTAC   55

    M  D  G  T  R  T  S  L  D  I  E  E  Y  S  D  T  E  V  Q
AGAAAAACCAAGTACTAACTCTGGAAGAATGGCAAGACAAGTGGGTGAACGGCAAGACTG  115
  K  N  Q  V  L  T  L  E  E  W  Q  D  K  W  V  N  G  K  T  A
CTTTTCATCAGGAACAAGGACATCAGCTATTAAAGAAGCATTTAGATACTTTCCTTAAAG  175
  F  H  Q  E  Q  G  H  Q  L  L  K  K  H  L  D  T  F  L  K  G
GCAAGAGTGGACTGAGGGTATTTTTTCCTCTTTGCGGAAAAGCGGTTGAGATGAAATGGT  235
  K  S  G  L  R  V  F  F  P  L  C  G  K  A  V  E  M  K  W  F
TTGCAGACCGGGGACACAGTGTAGTTGGTGTGGAAATCAGTGAACTTGGGATACAAGAAT  295
  A  D  R  G  H  S  V  V  G  V  E  I  S  E  L  G  I  Q  E  F
TTTTTACAGAGCAGAATCTTTCTTACTCAGAAGAACCAATCACCGAAATTCCTGGAACCA  355
  F  T  E  Q  N  L  S  Y  S  E  E  P  I  T  E  I  P  G  T  K
AAGTATTTAAGAGTTCTTCGGGGAACATTTCATTGTACTGTTGCAGTATTTTTGATCTTC  415
  V  F  K  S  S  S  G  N  I  S  L  Y  C  C  S  I  F  D  L  P
CCAGGACAAATATTGGCAAATTTGACATGATTTGGGATAGAGGAGCATTAGTTGCCATTA  475
  R  T  N  I  G  K  F  D  M  I  W  D  R  G  A  L  V  A  I  N
ATCCAGGTGATCGCAAATGCTATGCAGATACAATGTTTTCCCTCCTGGGAAAGAAGTTTC  535
  P  G  D  R  K  C  Y  A  D  T  M  F  S  L  L  G  K  K  F  Q
AGTATCTCCTGTGTGTTCTTTCTTATGATCCAACTAAACATCCAGGTCCACCATTTTATG  595
  Y  L  L  C  V  L  S  Y  D  P  T  K  H  P  G  P  P  F  Y  V
TTCCACATGCTGAAATTGAAAGGTTGTTTGGTAAAATATGCAATATACGTTGTCTTGAGA  655
  P  H  A  E  I  E  R  L  F  G  K  I  C  N  I  R  C  L  E  K
AGGTTGATGCTTTTGAAGAACGACATAAAAGTTGGGGAATTGACTGTCTTTTTGAAAAGT  715
  V  D  A  F  E  E  R  H  K  S  W  G  I  D  C  L  F  E  K  L
TATATCTACTTACAGAAAAGTAAATGAGACATAGATAAAATAAAATCACACTGACATGTT  775
  Y  L  L  T  E  K  *
```

FIG. 5A

TTTGAGGAATTGAAAATTATGCTAAAGCCTGAAAATGTAATGGATGAATTTTTAAAATTG 835
TTTATAAATCATATGATAGATCTTTACTAAAAATGGCTTTTTAGTAAAGCCATTTACTTT 895
TTCTAAAAAAGTTTTAGAAGAAAAAGATGTAACTAAACTTTTAAAGTAGCTCCTTTGGAG 955
AGGAGATTATGATGTGAAAGATTATGCCTATGTGTCTTGCAGATTGCAAGATATTTTACC 1015
AATCAGCATGTGTTACCTGTACAATTAAAAAAATATTTCAAAATGCAATGCATATTAAAT 1075
ATAATACACACAGAAAAACTGGCATTTATTTTGTTTTATTTTTTTGAGATGGAGTTTCGT 1135
TCTTGTTGCCCAACCTGGAGTGCAGTGGTGCGGTCTCGGCTCACTGCAACCTCTGCCTCC 1195
CGGGTTCGGGTGGTTCTCCTGCCTCGGCCTCCTGAGTGGCTGGGATTGCAGGTGTGCGCC 1255
ACCACGCCCGGCTAGTTTTTTGTGTTTTTAGTGGAGACGGGGTTTCACCATGTTGGTCAG 1315
GCTGATCTCGAGCTCCTGACCTCAGGTGATCTACCCACCTCGGCCTCCCAAAGTGCTGGG 1375
ATTACAGGCGTGAGCCACTGCACCTGGCCTGACATTCTTTATGAAATTTAGAATTGTTGA 1435
AGAACTATAACATTTCAGTAGGGTTCAAGGTGGTCCCAAAAGTTATATAAAAGATTAGTT 1495
TTTACTATAAACCCTTGTCTTTTACTCAGATCCTAGCATCCCTTTTCACATGGTTTCTCC 1555
ATGTATATAACAGAATCAAGAAACAAATTTTAATTAAACAATCTGTAACAGAATCAAGAA 1615
ACAAATACATTTTAATTAAACAATCTATATGGAACAAACATTCCCAAATTCTAAGAATAA 1675
ATTTTTCTTTAAGTTTTCTCTGAGTTTGGCAATTGTTGTTTTTTATAATTTAATCTGTTT 1735
AAATCATCAGGTCTTATAAAATATAATGTACTTAGAGCTGGATTCATGGCTGTTTATTAT 1795
GAAAGGTTAGATTTCTCAGTTCTTCTTTAACCACATTTTGTTATATCAGACAGTCCTCTA 1855
TAACTCTGTACTACCCAACAACTAAATGGTTTAGATTGTTTAGCTCATGTTAATAGGATG 1915
GTTGTGTATTATAAAAAACGAGTTACGTGTGTGTGTGCACGCATGCACGCACATGTGCTG 1975
GCTTAAAGGTTGTTAATGCAAGGTTTGGGGTCCCCTTTAACACTGGTGAAAGCTACGGTA 2035
CTCTCCCCAGAGATATGTCTTGTCAGCCTCTCTAGTTCCCCTTGGCCTGCATGTACAAAC 2095
TTCTACCCTAGAAGCTCTCTGCCATCGATGTATTCTAATAGATTTGTAAGGCTATTAATT 2155
TGAAGCAACTCCTTGCTCACAGTGATTCTTGCTTCTCTGAGACCTGCTCCCAGTCGATAC 2215
TGTGGGCTTCAGAAGCCATGACTCCCCAACTCTGCCTGTATCACCGGTTGAATGGACAAC 2275
TAACCCGAGCTGGACCAACACAATTCTCTCCAGAGACTTTTGATTTTACTTTTATGTAGA 2335
GACAGGGTCTCACTTTGTTGCCCACGCTGATGTTGAACTTGACGTGAGGCCTCAAGCAGT 2395
CCTCCTGTCTTGGCCACCCAAAGTGCTAGGATTACAGGTATGAGCCATTGCGCTGGCCCT 2455
CTTCATAGGCTTTTGGACTTGGGAATAGAAAAGCAACCCCGTCTCTACTGAAAGTGCAGA 2515
AGGATTGGCCGGGCGTGGTGGCGCGTGCCTGTGGTCCCAGCTGCTTGGGGGGCTGAGGCG 2575
GGAGAATCACTTGGACCTGGGGGGCGGAGGTTGCAGTGAGCTGAGATCGTGCCACTGCAC 2635
GCCAGCCTGGGCAACAGAGCAAGACTCTGTCTCAAAAGAAAG(A)$_{18}$

FIG. 5B

STABLY-TRANSFORMED CELLS EXPRESSING HUMAN THIOPURINE METHYLTRANSFERASE

This invention was made with the support of the National Institutes of Health under Grant Nos. GM 28157 and GM 35720. The U.S. Government has certain rights in the invention. This is a continuation of application Ser. No. 08/074,348, filed Jun. 9, 1993, now abandoned.

BACKGROUND OF THE INVENTION

Thiopurine methyltransferase (TPMT, EC 2.1.1.67) is a cytoplasmic enzyme that catalyzes the S-adenosyl-L-methionine (Ado-Met)-dependent S-methylation of aromatic and heterocyclic sulfhydryl compounds. See L. C. Woodson et al., *Biochem. Pharmacol.*, 32, 819 (1983); M. M. Ames et al., *J. Med. Chem.*, 29, 354 (1986). Included among the substrates for TPMT are the thiopurine drugs, 6-mercaptopurine (6-MP) and azathioprine. See, C. N. Remy et al., *J. Biol. Chem.*, 238, 1078 (1963). Mercaptopurine is an antimetabolite precursor that is used to treat a variety of leukemias, and as an immunosuppressive drug to treat arthritis, colitis and lupus. Azathioprine is a Class II immunosuppressive drug which is widely used in kidney transplantation.

The level of TPMT activity in human tissue is controlled by a common genetic polymorphism, and inherited variation in TPMT activity is an important factor responsible for individual differences in thiopurine drug toxicity and therapeutic efficacy. See, for example, P. R. Chocair et al., *Transplantation*, 53, 1051 (1992) and L. Lennerd, *Lancet*, 336, 225 (1990). As reported by R. M. Weinshilboum et al., *Am. J. Human Genet.*, 32, 651 (1980), phenotypic expression of the TPMT genetic polymorphism can be determined in an easily accessible human cell, the red blood cell (RBC). This polymorphism also controls the level of enzyme activity in all other human tissues and cells that have been studied, including liver, kidney and lymphocytes. Patients with genetically low or undetectable RBC TPMT activity are at greatly increased risk for the development of life-threatening thiopurine-induced myelosuppression when treated with azathioprine or 6-MP, while patients with high TPMT activity may be undertreated with standard doses of these drugs, since they can so readily deactivate them.

Although the level of activity of TPMT and the TPMT-mediated metabolism of bioactive substances can be studied using experimental animals, a continuing need exists for a stable in vitro model system for mammalian TPMT activity that can be used to rapidly and reproducibly evaluate and predict the pathways of TPMT-mediated drug metabolism in humans.

SUMMARY OF THE INVENTION

The present invention provides an isolated, purified DNA sequence encoding human thiopurine methyltransferase (TPMT), as well as isolated, purified human TPMT itself, which is a polypspride comprising 245 peptidyl ("amino acid") residues. The DNA sequence (TPMT cDNA) can be introduced into the genome of mammalian cell lines by in vitro techniques known to the art, to yield a transgenic mammalian cell line having the TPMT cDNA stably integrated into its genome, so that human TPMT activity is expressed by said cell line. Preferably, the transgenic cell line (and the parent, untransformed cell line) do not express significant autologous TPMT activity.

Preferably, the recombinant DNA sequence encoding human TPMT corresponds to the nucleotide sequence depicted in FIG. 5 (SEQ ID NO:1), and the human TPMT is a polypeptide having the amino acid sequence shown in FIG. 5 (SEQ ID NO:2). D. Ingrosso et al. in *J. Biol. Chem.*, 264, 20131 (1989) have reported that enzymes which utilize Ado-Met as a co-substrate contain three regions of sequence homology, designated I, II and III, that might be involved in Ado-Met binding. Region I was characterized further by G. Wu et al., in *J. Gen. Microbiol.*, 138, 2101 (1992), who reported that many, but not all, methyltransferase enzymes contain the sequence motif ΔΔD/EΔGXGXGXΔXXXΔΔ^ (SEQ ID NO:15), in which ^ indicates a hydrophobic amino acid, ^ indicates a polar or charged amino acid and X indicates any amino acid. On the basis of study of 12 mammalian cytoplasmic methyltransferases, T. Gomi et al., *Int. J. Biochem.*, 24, 1639 (1992) concluded that the "signature" sequence within region I described by Ingrosso et al. was L(D/E)OGSGSG (SEQ ID NO:16), in which O represents a hydrophobic amino acid and S a small neutral amino acid. In addition, Gomi et al. concluded that the signature sequence within region III reported by Ingrosso et al. was L(R/K)PGGXL (SEQ ID NO:17), in which X represents any amino acid. However, unexpectedly, the protein encoded by the TPMT cDNA of the present invention contains no amino acid sequences with 3 or fewer mismatches with the hypothetical region I Ado-Met binding sequence reported by Wu et al., and no sequences comparable to either the region I or region III signature sequences reported by Gomi et al.

The transgenic cell lines of the present invention provide the basis for an in vitro assay system which is effective to evaluate the susceptibility of a known or potential bioactive compound (or "drug") to TPMT-mediated metabolism. Thus, the present invention provides a method of determining the susceptibility of a compound to metabolism by human TPMT, comprising:

(a) adding a preselected amount of said compound to culture medium comprising a cultured transgenic mammalian cell line, the genome of which has been augmented by a chromosomally integrated recombinant DNA sequence, wherein said DNA sequence expresses mammalian TPMT, and wherein said transgenic cell line does not express autologous TPMT;

(b) determining at least one metabolite of said compound generated in the culture medium due to the exposure of said compound to said TPMT.

In accord with the present method, the metabolite(s) can be isolated, characterized, and further evaluated for toxicity and/or therapeutical activity.

Thus, the present method provides a rapid, reproducible and sensitive in vitro assay which is useful to predict the susceptibility of a given compound, i.e., a drug candidate, to TPMT-mediated metabolism, thus obviating the need to employ whole animal model systems or human subjects in phase I clinical trials, at least initially. A plurality of drugs, i.e., two or more drugs, can also be exposed to human TPMT activity in the present assay method, and their ability, if any, to compete for available TPMT activity can be determined, along with their actual metabolites. Also, preselected mutations in the TPMT cDNA sequence can be used to identify the molecular basis for the genetic polymorphism controlling the level of TPMT activity in human tissue.

In a preferred assay system, the recombinant DNA sequence expresses human TPMT, which is detected as TPMT activity in the culture medium, or in lysates of the transgenic cell line. Preferably, the mammalian cell line is a non-human cell line, e.g., is a murine or simian cell line. The recombinant DNA sequence is preferably a chimeric DNA sequence which further comprises a promoter which is functional in said mammalian cell line, to control the expression of the TPMT-encoding eDNA. The chimeric DNA sequence can further comprise a selectable marker gene or a reporter gene which permits the detection and/or selection of the transgenic cells in a population of cells subject to transformation from the untransformed cells in said population. Useful selectable marker genes impart resistance to an amount of a toxic agent which inhibits the growth of the corresponding untransformed cells. Preferably, a plasmid or viral vector comprising the recombinant DNA sequence is used to transfect a target mammalian cell line, but the isolated DNA sequence can also be introduced directly into mammalian target cells in vitro.

Polypeptides and nucleotide bases are depicted hereinbelow using standard single letter codes: A, alanine; R, arginine, N, asparagine; D, aspartic acid; C, cysteine; Q, glutamine; E, glutamic acid; G, glycine; H, histidine; I, isoleucine; L, leucine; K, lysine; F, phenylalanine; M, methionine; P, proline; S, serine; T, threonine; W, tryptophan, Y, tyrosine; V, valine, and polypeptides are read from the left (amino terminus) to the right (carboxyl terminus).

Other abbreviations used hereinbelow are as follows: sodium dodecylsulfate, SDS; polyacrylamide gel electrophoresis, PAGE; S-adenosyl-L-methionine, Ado-Met; S-adenosyl-L-homocysteine, Ado-Hcy; 6-mercaptopurine, 6-MP; 6-methylmercaptopurine, 6-MMP; Dulbecco's modified Eagle's medium, DMEM; phosphate buffered saline, PBS; polyvinylidene difluoride, PVDF; 3,4-dimethoxy-5-hydroxybenzoic acid, DMHBA; 2,3-dichloro-α-methylbenzylamine, DCMB; guanidinoacetate methyltransferase, GAMT; glycine methyltransferase, GMT; histamine N-methyltransferase, HNMT; hydroxyindole O-methyltransferase, HIOMT; protein carboxyl methyltransferase, PCMT; catechol 0-methyltransferase, COMT; and phenylethanolamine N-methyltransferase, PNMT.

BRIEF DESCRIPTION OF THE FIGURES

FIG. 1 depicts amino acid sequences of peptide fragments isolated after limited proteolysis of human kidney TPMT performed with papain (SEQ ID NO:3), *S. aureus* V8 protease (V8) (SEQ ID N0:4) or cyanogen bromide (CNBr) (SEQ ID NO:5, SEQ ID NO:6). Amino acid sequences obtained after limited proteolysis with papain and S. aureus V8 protease were overlapping. Residue 20 in the papain-*S. aureus* V8 protease amino acid sequence was unresolved and is indicated as "X". Residues 5 and 9 in the 5 kDa cyanogen bromide fragment could have been either of the amino acids indicated.

FIG. 5 depicts the T84 human colon carcinoma cell TPMT cDNA clone nucleotide sequence (SEQ ID NO:1). Underlined areas in the deduced amino acid sequence (SEQ ID NO:2) indicate sequences obtained by partial amino acid sequencing of human kidney TPMT (see FIG. 1). Underlined areas in the nucleotide sequences indicate sequences that were used to design PCR primers (see FIG. 2).

DETAILED DESCRIPTION OF THE INVENTION

Figure 2:
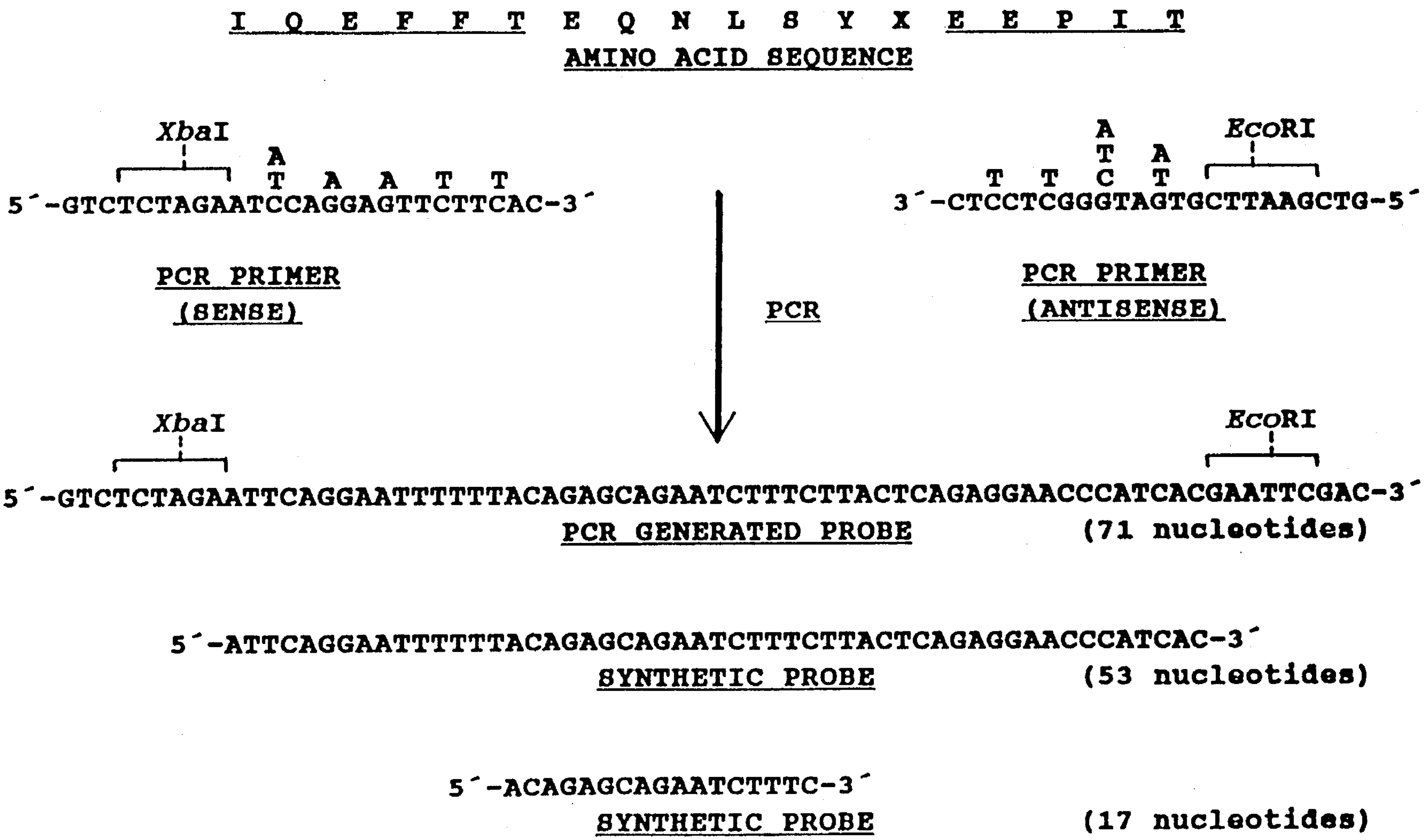
FIG. 2 is a schematic representation of the PCR-based strategy used to generate oligonucleotide probes for screening cDNA libraries. Sequentially, from top to bottom, the figure depicts use of the portions of the amino acid sequence (SEQ ID NO:7) determined after papain-*S. aureus* V8 protease treatment with the least degenerate genetic code to design degenerate PCR primers that include 9 additional nucleotides at the 5' and 3' ends which contained XbaI and EcoRI restriction sites, respectively (SEQ ID NO:8–SEQ ID NO:12).

TPMT catalyzes an important pathway in the biotransformation of thiopurine drugs. These drugs are used to treat transplantation patients who require immune suppression and patients with neoplastic disease such as acute lymphoblastic leukemia of childhood. Unfortunately, the therapeutic index of these thiopurine drugs is narrow, and their use can lead to life-threatening side effects such as myelosuppression. A. R. P. Patterson et al., in *6-Thiopurines, Antineoplastic and Immunosuppressive Agents,* A. C. Santorelli et al., eds., Springer-Vertag, N.Y. (1975) at p. 384–403. Approximately one in every 300 Caucasian subjects lacks TPMT on a genetic basis, and is even more at risk for the occurrence of severe myelosuppression when treated with standard doses of 6-MP or azathioprine. Furthermore, 11% of the population is heterozygous for this genetic polymorphism and may also require reduced doses of thiopurine drugs.

In order to provide a basis for determining the molecular origin for the genetic polymorphism in human TPMT activity, it is necessary to purify, to obtain partial amino acid sequence data for, and to clone and express cDNA for human TPMT. Therefore,, human kidney TPMT was purified, and the protein was subjected to limited proteolysis. Amino acid sequence data was obtained from the resultant peptide fragments by known sequencing techniques. Oligonucleotide primers based on the amino acid sequence information were used to amplify a unique sequence from human liver cDNA by the use of the polymerase chain reaction (PCR). As described hereinbelow, an oligonucleotide probe based on the sequence of the PCR product was used, unsuccessfully, to screen a human liver cDNA library.

Since TPMT has also been reported to be present in the colon, T84 human colon carcinoma cells were evaluated and were found to express TPMT activity with biochemical properties similar to those of the human kidney and liver TPMT. Oligonucleotide probes based on a partial human kidney TPMT amino acid sequence were then used to screen a T84 human colon carcinoma cell cDNA library. A 2.7 kb cDNA clone was isolated that contained an open reading frame of 735 nucleotides which encodes a protein of 245 amino acids. The deduced amino acid sequence of the encoded protein included one 24- and two separate 12-amino acid sequences identical to those obtained by sequencing proteolytic fragments of purified human kidney TPMT.

RNA transcripts were made in vitro from the open reading frame of the cDNA clone. These transcripts were translated in a rabbit reticulocyte lysate system, and the resulting translation product co-migrated with human kidney TPMT on SDS-PAGE. The T84 cell cDNA clone, truncated within the 3'-untranslated region at an SstI restriction site, was then used to create an expression construct with the eukaryotic expression vector P91023(B), and this construct was used to transfect primate COS-1 cells. The transfected cells transiently expressed a high level of TPMT enzymatic activity. This activity displayed a pattern of inhibition by TPMT inhibitors identical with that of human kidney and T84 human colon carcinoma cell TPMT.

Cloning of cDNA for this important drugmetabolizing enzyme may make it possible to define the molecular basis of the TPMT genetic polymorphism in humans. Because of the clinical significance of the pharmacogenetic regulation of TPMT, understanding the molecular basis of the genetic polymorphism is important both to define the mechanism of inherited variation in this enzyme activity and to provide clinically useful diagnostic tests, as described hereinabove. Isolated, purified preparations of mammalian TPMT are useful to catalyze the S-methylation of bioactive compounds and precursors to bioactive compounds in vitro, for synthetic purposes, and in order to study and mimic metabolic pathways.

The present invention also provides a transgenic cell line having a genome augmented by a recombinant ("non-native") DNA sequence, preferably a chromosomally integrated recombinant DNA sequence, which comprises a gene encoding mammalian thiopurine methyltransferase (TPMT), which cell line further does not express significant autologous or "native" TPMT.

A preferred embodiment of the present invention is a transgenic mammalian cell line which contains chromosomally integrated, recombinant ("genetically-engineered") DNA, which DNA expresses human TPMT, but does not express autologous TPMT. The cell line is preferably of human or primate origin, such as the exemplified monkey kidney COS cell line, but cell lines derived from other species may be employed, including chicken, hamster, murine, ovine and the like.

As used herein with reference to the present invention, the term "cell line" is intended to refer to well-characterized homogeneous, biologically pure populations of cells, preferably mammalian cells, which are neoplastic or which have been "immortalized" in vitro by methods known to the art.

"Transgenic" is used herein to include any cell or cell line, the genome of which has been altered or augmented by the presence of at least one recombinant DNA sequence, which DNA is also referred to in the art of genetic engineering as "heterologous DNA," "exogenous DNA," "genetically engineered," "non-native," or "foreign DNA," wherein said DNA was isolated in vitro introduced into the genome of the cell or cell line by a process of genetic engineering.

As used herein, the term "recombinant DNA" refers to DNA that has been derived or isolated from any appropriate tissue source, that may be subsequently chemically altered in vitro, and later introduced into mammalian cells. An example of recombinant DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome which is the recipient of the DNA, or it is resident in the genome but is not expressed.

The recombinant DNA sequence, used for transformation herein, may be circular or linear, double-stranded or single-stranded. Generally, the DNA sequence is in the form of chimeric DNA, such as plasmid DNA, that can also contain coding regions flanked by regulatory sequences which promote the expression of the recombinant DNA present in the resultant cell line. For example, the recombinant DNA may itself comprise a promoter that is active in mammalian cells, or may utilize a promoter already present in the genome that is the transformation target. Such promoters include the CMV promoter, as well as the SV 40 late promoter and retroviral LTRs (long terminal repeat elements).

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual,* Cold Spring Harbor Laboratory Press (2d ed., 1989), provides suitable methods of construction.

Aside from recombinant DNA sequences that serve as transcription units for TPMT or portions thereof, a portion of the recombinant DNA may be untranscribed, serving a regulatory or a structural function.

The recombinant DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in mammalian cells. Useful selectable markers are well known in the art and include, for example, antibiotic and herbicide-resistance genes, such as neo, hpt, dhfr, bar, aroA, dapA and the like.

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli,* the beta-glucuronidase gene (gus) of the uidA locus of *E. coli,* and the luciferase gene from firefly *Photinus pyralis.* Expression of the reporter gene is assayed at a suitable time after the DNA has been introduced into the recipient cells.

Other elements functional in mammalian cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like.

Such elements may be included in the DNA as desired to obtain the optimal performance of the transforming DNA in the cell.

The recombinant DNA can be readily introduced into the target cells by transfection with an expression vector comprising cDNA encoding TPMT by the modified calcium phosphate precipitation procedure of C. Chen et al., *Mol. Cell. Biol.*, 7, 2745 (1987). Transfection can also be accomplished by lipofection, using commercially available kits, e.g., provided by BRL.

The present invention also provides purified, isolated thiopurine methyltransferase, which can be prepared by recombinant DNA methodologies as disclosed hereinbelow. However, since the present invention provides the amino acid sequence of human TPMT (FIG. 5), TPMT or bioactive analogs thereof can also be synthesized by the solid phase peptide synthesis (or Merrifield) method. This established and widely used method, including the experimental procedures, is described in the following references: Stewart et al., *Solid Phase Peptide Synthesis*, W. H. Freeman Co., San Francisco (1969); Merrifield, *J. Am. Chem. Soc.*, 85, 2149 (1963); Meienhofer in "Hormonal Proteins and Peptides," ed; C. H. Li, Vol 2 (Academic Press, 1973), pp. 48–267; and Barany and Merrifield in "The Peptides," eds. E. Gross and F. Meinenhofer, Vol. 2 (Academic Press, 1980), pp. 3–285. The synthesis is commenced from the carboxyterminal end of the peptide using an alpha-amino protected amino acid. Fluorenylmethyloxy-carbonyl (Fmoc) or t-butyloxycarbonyl (Boc) protective groups can be used for all amino groups even through other protective groups are suitable, and the first protected amino acids can be esterified to chloromethylated polystyrene resin supports. The polystyrene resin support is preferably a copolymer of styrene with about 0.5 to 2% divinyl benzene as a crosslinking agent which causes the polystyrene polymer to be insoluble in certain organic solvents. See Carpino et al., *J. Org. Chem.*, 37, 3404 (1972); Meinhofer, *Int. J. Pept. Pro. Res.*, 11, 246 (1978); and Merrifield, *J. Am. Chem. Soc.*, 85, 2149 (1963). These and other methods of peptide synthesis are also exemplified by U.S. Pat. Nos. 3,862,925; 3,842,067; 3,972,859; 4,105,602 and 4,757,048.

The immobilized peptide is then N-deprotected and other amino acids having protected amino groups are added in a stepwise manner to the immobilized peptide. At the end of the procedure, the final peptide is cleaved from the resin, and any remaining protecting groups are removed, by treatment under acidic conditions such as, for example, with a mixture of hydrobromic acid and trifluoroacetic acid or with hydrofluoric acid, or the cleavage from the resin may be effected under basic conditions, for example, with triethylamine, the protecting groups then being removed under acid conditions.

The cleaved peptide is isolated and purified by means well known in the art such as, for example, lyophilization followed by either exclusion or partition chromatography on polysaccharide gel media such as Sephadex G-25, or countercurrent distribution. The composition of the final peptide may be confirmed by amino acid analysis after degradation of the peptide by standard means.

The synthesis may use manual techniques or be completely automated, employing, for example, an Applied BioSystems 431A Peptide Synthesizer (Foster City, Calif.) or a Biosearch SAM II automatic peptide synthesizer (Biosearch, Inc., San Rafael, Calif.), following the instructions provided in the instruction manual and reagents supplied by the manufacturer. Disulfide bonds between Cys residues can be introduced by mild oxidation of the linear peptide by KCN as taught in U.S. Pat. No. 4,757,048 at Col. 20.

Salts of carboxyl groups of the TPMT peptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the polypeptides may be prepared by contacting the polypeptide with one or more equivalents of the desired inorganic or organic acid, such as, for example, hydrochloric acid.

Esters of carboxyl groups of the polypeptides may be prepared by any of the usual methods known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus, the C-terminal end of the peptide when freed from the resin is directly esterified without isolation of the free acid.

Amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

In addition, these peptide sequences can be modified by substituting one or two conservative amino acid substitutions for the positions specified, including substitutions which utilize the D rather than L form. As these peptides can be synthesized using standard solid-phase techniques, for example, it is not necessary to confine the conservative substitutions to amino acids encoded by genes.

The invention is also directed to modified forms of the TPMT polypeptides encoded by the cDNA of FIG. 5. One or more of the residues of this polypeptide can be altered, so long as activity is retained. Conservative amino acid substitutions are preferred—that is, for example, aspartic-glutamic as acidic amino acids; lysine/arginine/histidine as basic amino acids; leucine/isoleucine, methionine/valine as hydrophobic amino acids; serine/glycine/alanine/threonine as hydrophilic amino acids. However, as the peptides need not be prepared by recombinant methods or from the gene, the substitutions may include nonencoded amino acids such as the D- or beta-amino forms.

Therefore, reference to mammalian TPMT having an amino acid sequence corresponding substantially to the amino acid sequence shown in FIG. 5 is intended to refer to an amino acid sequence encoded by DNA that hybridizes to the TPMT encoding cDNA of FIG. 5 under conditions corresponding to the stringency represented by hybridization in buffer containing 20% formamide, 5×Denhardt's (0.5 g Ficoll 400, 0.5 g polyvinylpyrrolidone, and 0.5 g bovine serum albumin (Pentax fraction V) per 500 ml $H_2O$), 6×SSC, 100 mg/ml RNA and 0.05% sodium pyrophosphate at 42° C., followed by washing at 60° C. at 1×SSC, 0.1% SDS. In addition, the TPMT encoded by this DNA must exhibit at least 80–90% of the enzymatic activity of human TPMT as disclosed hereinbelow. Of course, the ability of another DNA to hybridize to the cDNA of FIG. 5 also defines other DNA sequences which are "substantially equivalent" to the cDNA of FIG. 5.

The invention will be further described by reference to the following detailed examples wherein [$^3$H-methyl]-Ado-Met (84.3 mCi/μmole) and [$^{14}$C-methyl]-Ado-Met (58.0 μCi/μmole) were purchased from DuPont-NEN (Boston, Mass.). [γ-$^{32}$P]dATP (>7000 Ci/mmol) was obtained from ICN Biomedicals, Inc. (Costa Mesa, Calif.). [α-$^{35}$S]dATP (>1000 Ci/mmol) and [α-$^{32}$P]dCTP (>3000 Ci/mmol) were purchased from Amersham Corp. (Arlington Heights, Ill.). $T_4$ polynucleotide kinase, DNA ligase, murine reverse transcriptase, DMEM, Ham's F-12 media and fetal calf serum were obtained from GIBCO BRL (Gaithersburg, Md.). Restriction enzymes were purchased from GIBCO BRL and Boehringer Mannheim Corp. (Indianapolis, Ind.). DEAE-Sepharose CL-6B, Sephadex G-100 Superfine and DEAE-dextran were obtained from Pharmacia LKB Biotechnology, Inc. (Piscataway, N.J.). Hydroxylapatite and tricine were purchased from Calbiochem (San Diego, Calif.). Low molecular weight protein markers, SDS-PAGE reagents and Bio-Rad Protein Assay Dye Reagent were obtained from Bio-Rad Laboratories (Richmond, Calif.). Allopurinol, bovine serum albumin, dithiothreitol, S-adenosyl-L-homocysteine (Ado-Hcy) HCl, Ado-Met HCl, 6-MP, 6-MMP, cyanogen bromide, *S. aureus* V8 protease, papain, and salmon testis DNA were purchased from Sigma Chemical Co. (St. Louis, Mo.). 3,4-Dimethoxy- 5-hydroxybenzoic acid (DMHBA) was obtained from ICN Pharmaceuticals, Inc. (Plainview, N.Y.). Amodiaquine-HCl was donated by Warner Lambert Co. (Ann Arbor, Mich.), SKF-525A was a gift from Dr. R. Van Dyke, Henry Ford Medical Center (Detroit, Mich.) and 2,3-dichloro-α-methylbenzylamine (DCMB) was obtained from Research Biochemical, Inc. (Natick, Mass.). RESOLUTION™ autoradiogram enhancer was purchased from F. M. Corporation (Chestnut Hill, Mass.). A low range molecular weight marker kit was obtained from Diversified Biotech (Newton Centre, Mass.) and Immobilon-PVDF membranes were purchased from Millipore Corporation (Bedford, Mass.).

Photoaffinity labeling of TPMT with [$^3$H-methyl]-Ado-Met confirmed that the approximate molecular mass of TPMT was 35 kDa as estimated by SDS-PAGE. The amino terminus of the enzyme was blocked to Edman degradation. Therefore, limited proteolysis was performed to generate peptide fragments that could be used in amino acid sequencing. When enzymatic proteolysis was performed on human kidney TPMT Peak 1 by the method of D. W. Cleveland et al., *J. Biol. Chem.*, 252, 1102 (1977), 50–100 μg of human kidney TPMT peak I (partially purified by gel filtration or hydroxy apatite chromatography) was placed on a 10% polyacrylamide-SDS slab gel, electrophoresis was performed as described by U. K. Laemmli, *Nature* (London), 227, 680 (1970) proteins were visualized with Coomassie Blue, TPMT protein was excised in gel slices, and slices were placed in the wells of a 15% polyacrylamide-SDS gel together with proteolytic enzyme. The location of TPMT on the initial gel was verified by electrophoresis of enzyme photoaffinity labeled with [$^3$H-methyl]-Ado-Met.

The proteases used in these experiments included *Staphylococcus aureus* V8 protease (0.03 μg/well) and papain (0.2 μg/well). Proteolysis times prior to electrophoresis were 30 min for *S. aureus* V8 protease and 12 hr for papain. The peptide fragments generated during proteolysis were separated by SDS-PAGE and were transferred by the method of H. Towbin et al., *PNAS USA,* 76, 4350 (1979) to polyvinylidene difluoride (PVDF) membranes for 3 hr at 80 vols in 192 mM glycine, 25 mM Tris, pH 8.3, and 15% methanol. The PVDF membranes were stained with. 0.5% Coomassie Blue in 40% methanol, followed by destaining with 50% methanol.

Proteolysis was also performed by cyanogen bromide cleavage by the method of W. Jahnen et al., *Biochem. Biophys. Res. Commun.*, 166, 139 (1990). In those experiments, 100–200 μg of partially purified TPMT was subjected to SDS-PAGE, and individual proteins were excised in gel slices and were dried by lyophilization. The polypeptides from the dried gel slices were electroblotted onto PVDF membranes and sequenced with either a Proton 2090E Integrated Microsequencing system (Proton Instruments Inc., Tarzana, Calif.) or with an ABI 470A/120A Microsequencer (Applied Biosystems Inc., Foster City, Calif.) using on-line reverse phase HPLC performed with narrow bore $C_{18}$ columns. Data were collected with an Everex 286/12 computer and were analyzed using Proton Instruments protein sequence analysis software.

The University of Wisconsin Genetics Computer Group software package was used to analyze sequence information and to make comparisons between the sequence of the TPMT cDNA clone and the sequences of other cloned proteins. The GenBank Genetics Sequence Data Bank and the EMBL Nucleotide Sequence Database were used to search for nucleotide homologies, whereas the Swiss-Prot Protein Sequence Database was used to search for protein structural homologies. $IC_{50}$ values were calculated with the GraphPAD Inplot program (GraphPAD, San Diego, Calif.).

Example 1

Protein Purification, Limited Proteolysis, and Partial Amino Acid Sequence of TPMT Renal tissue was obtained either during autopsy or from patients undergoing clinically indicated nephrectomies. Hepatic tissue was obtained from patients who underwent clinically indicated partial hepatectomies for the removal of primary or metastatic hepatic tumors. All tissue was obtained under guidelines approved by the Mayo Clinic Institutional Review Board. Macroscopically normal tissue was stored at −80° C., conditions under which TPMT activity is stable (C. L. Szumlanski et al., *Pharmacogenetics,* 2, 148 (1992); J. A. Van Loon et al., *Drug Met. Disposit.*, 18, 632 (1990)). Prior to enzyme purification, renal tissue was homogenized in 5 mM potassium phosphate buffer, pH 7.5, with a Polytron homogenizer, and a 100,000×g supernatant was prepared as described by L. C. Woodson et al., *Biochem. Pharmacol.*, 32, 819 (1983). Amino acid sequence information was obtained with TPMT purified from human renal tissue—a tissue with a high specific activity for the enzyme.

Human renal tissue contains two isoforms of TPMT, Peak I and Peak II, that can be separated by DEAE ion exchange chromatography as reported by J. A. Van Loon et al., *Biochem. Genet.*, 20, 637 (1982). The two isoforms were separated by DEAE ion exchange chromatography, and the Peak I enzyme was then purified by gel filtration chromatography performed with Sephadex G-100 superfine as described by J. A. Van Loon et al., cited above. In some experiments, hydroxylapatite chromatography performed as described by J. A. Van Loon et al., in *Biochem. Pharmacol.*, 44, 775 (1992) was added as a third purification step.

TPMT activity in renal tissue was measured by the method of R. M. Weinshilboum et al., in *Clin. Chim. Acta*, 85, 323 (1978) as modified by L. C. Woodson et al., *Biochem. Pharmacol.*, 32, 819 (1983) to assay the enzyme in human kidney preparations. The assay is based on the conversion of 6-MP to radioactively-labeled 6-methylmercaptopurine (6-MMP) with [$^{14}$C-methyl] Ado-Met as the methyl donor. Assay conditions for the measurement of TPMT in T84 human colon carcinoma cells and in COS-1 cells were identical with those used to measure the enzyme activity in human renal tissue. One unit of TPMT activity represented the formation of 1 nmol of 6-MMP per hr of incubation at 37° C.

Cyanogen bromide cleavage yielded two peptides that did not have blocked amino termini and were present in adequate quantity for amino acid sequencing, one 5 kDa and the other 19 kDa in apparent molecular mass. Each of these fragments yielded a sequence of 12 amino acids which is depicted in FIG. 1. The 21 kDa fragment generated by papain and the 18 kDa fragment generated by *S. aureus* V8 protease contained the overlapping amino acid sequences shown in FIG. 1. Combined information obtained from these two fragments yielded a sequence of 25 amino acids with one unresolved residue, (designated "X" in FIG. 3). This amino acid sequence information from the protease enzymatic cleavage was then used to design an oligonucleotide probe for use in screening cDNA libraries.

Example 2

Screening Human Liver cDNA Library

TPMT is highly expressed in human kidney, liver and colon. Initially, a human liver cDNA library was screened. Total RNA was isolated from a frozen sample of human liver by extraction with guanidine HCl, followed by centrifugation through CsCl as taught by J. Sambrook et al., *Molecular Cloning: A Laboratory Manual,* C. Nolan, ed., Cold Spring Harbor Press (2d ed., 1989). First-strand cDNA for use as a template for PCR was synthesized with an oligo (dT) primer and murine reverse transciptase. Oligonucleotide primers for PCR were designed on the basis of amino acid sequence information obtained after limited proteolysis of TPMT. As depicted in FIG. 2, the amino acid sequence IQEFFT was used to design a sense primer containing all possible codons as well as an XbaI restriction site [5'-GTCTCTAGAAT(A/C/T)CA(A/G)GA(A/G)TT(T/C)TT(T/C)AC-3'] (SEQ ID NO:8). The amino acid sequence EEPIT (SEQ ID NO:18) was used to design an antisense primer containing all possible codons and an EcoRI restriction site [5'-GTC-GAATTCGT(A/G/T)AT(A/G/C/T)GG(C/T)TC(C/T)TC-3'] (SEQ ID NO:9).

The PCR reaction was performed in a 100 μl reaction volume (10 mM Tris, ph 8.3; 50 mM KCl; 1.5 mM $MgCl_2$; 0.01% gelatin; 50 μM for each of the four deoxynucleoside triphosphates; 4 μM for each primer; and 1 unit of *Thermus aguaticus* polymerase) in a Perkin Elmer Cetus DNA thermal cycler (Emeryville, Calif.). The amplification conditions used were 30 cycles of 1 min at 94° C., 1 min at 46° C., and 1 min at 72° C., followed by a final 10 min incubation at 72° C. The PCR reaction mixture was then applied to an 8% polyacrylamide gel, and PCR products were visualized by ethidium bromide staining.

A 71 nucleotide PCR product (SEQ ID NO:10) of approximately the predicted size was excised from the gel, and DNA was isolated with the MerMaid kit (BIO 101, Inc., La Jolla, Calif.). Because the recovery of DNA from the polyacrylamide gel after the initial cycle of amplification was low, the reaction was repeated using the 71 nucleotide species as template.

The product of the second cycle of amplification was applied to a 2.5% agarose gel, the 71 nucleotide PCR product was excised from the gel, and DNA was isolated using the MerMaid kit. She ends of the PCR product were filled in by use of the Klenow fragments of DNA polymerase, the product was ligated into the SmaI site of pBluescript (Stratagene, La Jolla, Calif.), and the plasmid was used to transform *Escherichia coli* DH5α made competent by the method of D. Hanahan, *J. Mol. Biol.*, 166, 557 (1983). The insert present in positive clones was sequenced by the dideoxy method of F. Sanger et al., *PNAS USA*, 74, 5463 (1977) with the $^{35}$S-sequencing protocol of the Sequenase kit version 2.0 (United States Biochemical Corp., Cleveland, Ohio).

The 71 nucleotide PCR products encode the amino acid sequence generated by papain-*S. aureus* V8 protease treatment of TPMT (FIG. 2). The previously unresolved residue ("X" in FIG. 1) was found to be serine. A non-degenerate 53 nucleotide probe (SEQ ID NO:11) based on the entire sequence of the PCR product, minus the restriction sites, was then synthesized (FIG. 2). This oligonucleotide probe was used to screen a human liver cDNA library constructed in the Uni-Zap XR vector (Stratagene, La Jolla, Calif.). The oligonucleotide probe was end-labeled with [γ-$^{32}$P] dATP by the procedure of J. Sambrook et al., *Molecular Cloning,* cited above.

Approximately one million plaque-forming units were screened from each library. Plaques were transferred to nitrocellulose filters, and hybridization was performed at 46° C. for 40 hr as described by Sambrook et al., in *Molecular Cloning.*

Although 2 clones remained positive through tertiary screening, DNA sequencing revealed that neither of them encoded amino acid sequences obtained after limited proteolysis of TPMT. Therefore, a T84 human colon carcinoma cell cDNA library was also screened. However, it was first necessary to determine whether these cells expressed TPMT.

Example 3

Expression of TPMT by T84 Cells

T84 human colon carcinoma cells (American Type Culture Collection, Rockville, Md.) were grown to confluence in an equal volume mixture of Dulbecco's modified Eagle's medium (DMEM) and Ham's F12 media with 5% fetal calf serum. The cells were then harvested, cell pellets were washed in phosphate buffered saline (PBS), and the pellets were homogenized for 30 sec in 1 ml of 5 mM potassium phosphate buffer, pH 7.5, with a Polytron homogenizer. Homogenates of the cells were centrifuged at 100,000×g for 1 hr at 4° C., and the supernatant was used to assay TPMT activity and to determine selected biochemical properties of the enzyme.

Cytosol from T84 cells did contain TPMT enzymatic activity. The optimal pH for assay of TPMT activity in these preparations was determined in the presence of 150 mM potassium phosphate buffer at seven different buffer pH values from 5.5 to 8.5. Optimal activity for T84 cell TPMT, like that of human kidney and liver TPMT, was present at pH 6.5, and apparent $K_m$ values of T84 cell TPMT for the two substrates for the TPMT reaction, 6-MP and Ado-Met, were then determined, and are shown on Table 1.

TABLE 1

TPMT
Biochemical Characteristics in Human Tissue

| Tissue | pH Optimum | Apparent $K_m$ Values 6-MP, mM | Apparent $K_m$ Values Ado-Met, μM | DMHBA $IC_{50}$, μM |
|---|---|---|---|---|
| T84 Cells | 6.5 | 0.71 | 5.1 | 6.6 |
| Human Liver | 6.5 | 0.58 | 2.7 | 8.5 |
| Human Kidney | 6.5 | 0.30 | 2.7 | 7.8 |

The human liver data shown on Table 1 were reported by C. L. Szumlanski et al., *Pharmacogenetics,* 2, 148 (1992) and the human kidney data, with the exception of the $ICa_{50}$ value for DMHBA, were reported by L. C. Woodson et al., *Biochem. Pharmacol.,* 32, 819 (1983).

Figure 3A:
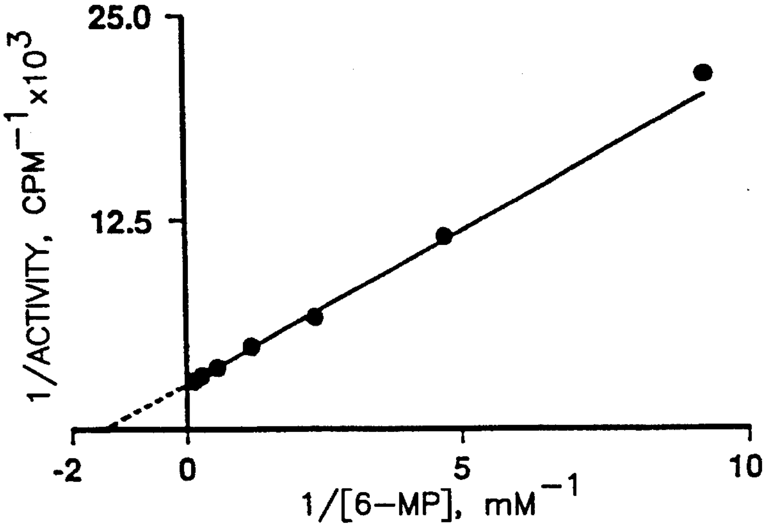
FIG. 3 depicts three plots used to evaluate T84 human colon carcinoma cell TPMT enzymatic activity: (A) double inverse plot of the relationship between TPMT activity and 6-MP concentration; (B) double inverse plot of the relationship between TPMT activity and Ado-Met concentration; and (C) DMHBA inhibition of T84 cell (●) and human kidney TPMT (○) enzymatic activities.
Figure 3B:
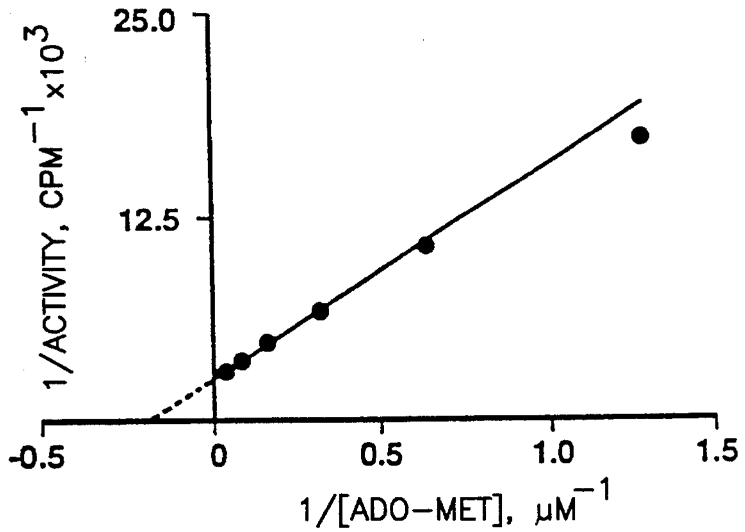
Figure 3C:
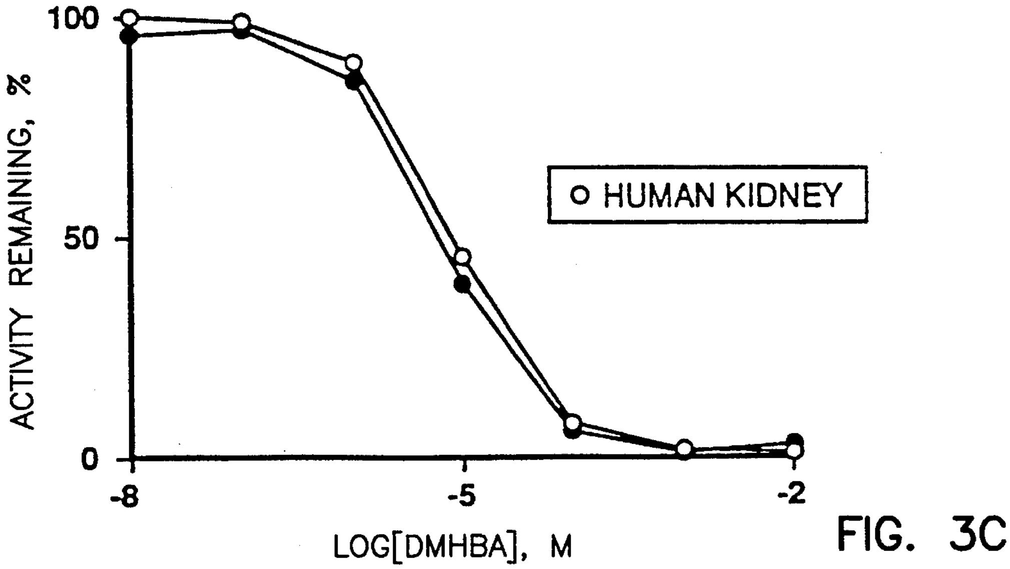

When enzyme activity was measured in the presence of 25 μM Ado-Met and seven concentrations of 6-MP that varied from 0.11 to 6.8 mM, an apparent $K_m$ value of 0.71 mM for 6-MP was calculated from the plot of FIG. 3 (Panel A). This value was similar to those that have been reported for human liver and kidney TPMT as shown on Table 1. When an apparent $K_m$ value for Ado-Met was calculated on the basis of data obtained in the presence of 3.4 mM 6-MP and six concentrations of Ado-Met that varied from 0.78 to 25 μM as plotted in FIG. 3, Panel B, a value of 5.1 μM was calculated. This $K_m$ value was similar to, but slightly higher, than those reported for human kidney and liver TPMT as shown on Table 1.

Finally, human kidney and liver TPMT activities are known to be inhibited by DMHBA (C. T. Szumlanski et al., cited above; L. C. Woodson et al., *Mol. Pharmacol.,* 24, 471 (1983)). $IC_{50}$ values for inhibition of T84 cell and human kidney TPMT by DMHBA were calculated on the basis of data obtained in the presence of seven concentrations of DMHBA that varied from 0.01 μM to 10 mM as plotted in FIG. 3, Panel C. The $IC_{50}$ values calculated from these data were 6.6 and 7.8 μM for T84 cell and human kidney TPMT, respectively. Therefore, T84 cells expressed TPMT activity, and the biochemical properties of this enzyme were very similar to those of TPMT in other human tissues.

Example 4

Screening a T84 Human Colon Carcinoma cDNA Library

Figure 4:
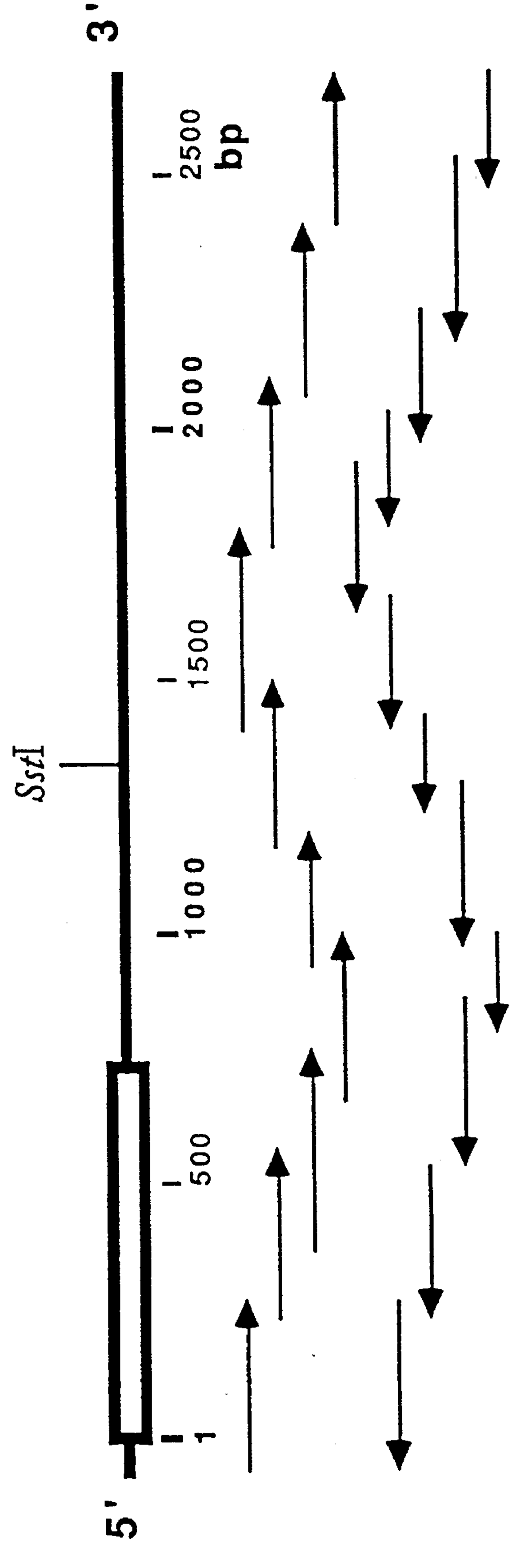
FIG. 4 is a schematic depiction of T84 human colon carcinoma cell TPMT cDNA. The open reading frame is represented as an open box. Arrows indicate DNA sequencing primers. The SstI restriction site used for creating an expression construct is shown.

A T84 human colon carcinoma cell cDNA library was screened with the 53 nucleotide probe shown in FIG. 4. Of the clones that were initially positive, five clones from the T84 cell library remained positive through secondary screening. Tertiary screening of these clones was performed with both the nondegenerate 53 nucleotide probe and with a nondegenerate 17 nucleotide probe, [5'-ACAGAGCA-GAATCTTTC-3'] (SEQ ID NO:12), the sequence of which was based on the nonprimer-dependent region of the 71 nucleotide PCR product (FIG. 2). One clone from the T84 cell library remained positive when screened with both probes. This clone was excised from Uni-Zap XR in vivo and was sequenced with the Sequenase kit version 2.0.

This clone was sequenced in both directions (FIG. 4) and was found to consist of 2760 nucleotides including an open reading frame of 735 nucleotides that encoded a protein of 245 amino acids (FIG. 5). All of the TPMT amino acid sequences obtained after limited proteolysis of the enzyme (FIG. 1) were encoded within the open reading frame. The T84 TPMT cDNA clone had a long 3'-untranslated region that terminated with a poly(A) tract. No consensus polyadenylation signal was present immediately upstream of the poly(A) region. The 3'-untranslated region contained two ALU-type repetitive elements. One of these elements was oriented 5' to 3' from nucleotides 2567 to 2695, while the other was oriented 3' to 5' from nucleotides 1101 to 1225. Finally, the predicted molecular mass of the protein encoded by the open reading frame was 28.2 kDa—less than the 35 kDa apparent molecular mass of TPMT estimated on the basis of SDS-PAGE of the photoaffinity labeled human kidney enzyme (J. A. Van Loon et al., *Biochem. Pharmacol.,* 44, 775 (1992) (see FIGS. 1 and 2)). The next step involves expression of the cDNA to determine whether the encoded protein has an apparent molecular mass similar to that of native human TPMT during SDS-PAGE and to determine whether it catalyzes the TPMT enzymatic reaction.

Example 5

In Vitro Transcription and Translation

The coding region of the T84 cell cDNA clone was amplified by PCR from the −5 nucleotide to nucleotide +739 with the addition of EcoRI restriction sites at each end. The primers used were [5'-GAATTCAAACCATGGATGGTA-CAAGAACT-3'] (SEQ ID NO:13) at the end of 5' end, and the antisense primer [5'-GAATTCTCATTTACTTTTCTG-TAAGTAGAT-3'] (SEQ ID NO:14) at the 3' end of the coding region. The single nucleotide underlined in the 5' end primer was changed from T to C to enhance translation efficacy, as suggeseted by M. Kozak, *J. Biol. Chem.,* 266,. 19867 (1991). The PCR conditions used were the same as those described hereinabove except that 100 ng of the cDNA clone served as template, 100 ng of each primer was used, and amplification conditions involved 35 cycles of 1 min at 94° C., 2 min at 50° C., and 3 min at 72° C., followed by a final 10 min incubation at 72° C.

The crude PCR reaction mixture was then applied to a 1% agarose gel, and the PCR products were visualized by ethidium bromide staining. A PCR product of 756 nucleotides was excised from the gel, and DNA was isolated with the GeneClean Kit (BIO 101, Inc., La Jolla, Calif.). The ends of the PCR product were filled in by use of the Klenow fragment of DNA polymerase. The product was then ligated into the SmaI site of pBluescribe, and this construct was used to transform *E. coli* DH5α made competent by the method of D. Hanahan, *J. Mol. Biol.,* 166, 557 (1983).

The insert present in positive clones was sequenced with the Sequenase kit version 2.0 to determine its orientation. The clone was then linearized with SstI, and T7 RNA transcripts were synthesized using the mCAP capping kit (Stratagene, La Jolla, Calif.).

These RNA samples were translated in vitro with a rabbit reticulocyte lysate system by the method of H. R. R. Pelham et al., *Eur. J. Biochem.,* 67, 247 (1976). Translated proteins were analyzed by SDS-PAGE together with a standard which consisted of human kidney TPMT Peak I that had been photoaffinity labeled with [$^3$H-methyl]-Ado-Met, as disclosed by J. A. Van Loon et al., *Biochem. Pharmacol.,* 44, 775 (1992). The major translation product of this RNA co-migrated during SDS-PAGE with the photoaffinity labeled human kidney TPMT with an apparent molecular mass of 35 kDa. Therefore, the 28.2 kDa protein encoded by the T84 TPMT cDNA clone behaved as if its molecular mass was approximately 35 kDa during SDS-PAGE.

Example 6

Expression of TPMT Activity with COS-1 Cells. Expression in COS-1 Cells

The cDNA clone of Example 5 was digested with SstI to excise the coding region, the 5'-untranslated region and a portion (ca. 600 nucleotides) of the 3'-untranslated region (FIG. 5). This insert was ligated into pBluescribe to create a second EcoRI site at the 3' end. This insert in the pBluescribe vector was deposited in the American type Culture Collection, Rockville, Md., under the provisions of the Budapest Treaty, and assigned ATCC Accession Number 75472. The pBluescribe clone was then digested with EcoRI, and the insert was cloned into the EcoRI site of the expression vector P91023(B) (G. G. Wong et al., *Science,* 228, 810 (1985); R. J. Kaufman et al., *PNAS USA,* 82, 689 (1985)). Positive P91023(B) clones were isolated by colony screening performed with the SstI fragment of the TPMT clone that had been radioactively labeled with random primers (See, J. Sambrook et al., *Molecular Cloning,* cited above), and the orientation of the insert was determined by partial restriction mapping and partial sequencing.

The "sense" expression constructs were designated A3 and A6, whereas constructs that contained the coding region in the antisense orientation were designated A1 and A2.

Simian COS-1 cells were then plated in 100-mm dishes at a density of 1.5–1.8×$10^6$ cells/dish in DMEM with 10% fetal calf serum, and were allowed to grow overnight. Three dishes of cells were used for each transfection. Purified "sense" plasmid vector (0.5 μg) was mixed with DEAE-dextran and DMEM, and the mixture was added to the cell culture dishes, following the procedures of J. H. McCutchan et al., *J. Natl. Cancer Inst.,* 41, 351 (1988) and R. J. Kaufman et al., *Mol. Cell. Biol.,* 9, 946 (1989). Control cells were treated with no DNA, with expression vector alone, or with constructs that contained the cDNA clone in an antisense orientation. After 1 hr, the DNA-DEAE-dextran solution was replaced for 2 min with DMEM that contained 10% dimethylsulfoxide, followed by incubation for 2 hr in 0.1 mM chloroquine in DMEM following the procedure of H. Luthman et al., *Nucl. Acids Res.,* 11, 1295 (1983). Cells were then grown for 40–42 hr in DMEM with 10% fetal calf serum. The cells from each transfection were harvested and pooled, cell pellets were washed in 5 ml of PBS, and the cell pellets were homogenized for 30 sec in 2 ml of 5 mM potassium phosphate buffer, pH 7.5. Homogenates were centrifuged at 15,000×g for 15 min at 4° C., supernatants from that step were centrifuged at 100,000×g for 1 hr at 4° C., and 0.25 μl aliquots of 100,000×g supernatant preparations were then assayed for transient expression of TPMT enzymatic activity. There was no increase in the low basal level of TPMT activity in COS-1 cells transfected with vector alone or with antisense constructs (Table 2). However, COS-1 cells transfected with the cDNA clone in the proper orientation had a greater than 100-fold increase in TPMT activity (Table 2).

TABLE 2

| Cell Line | TPMT Activity (units/mg protein) Experiment 1 | Experiment 2 |
|---|---|---|
| Control, no DNA | 4 | 5 |
| Control, P91023(B) | 4 | 5 |
| Control, A1 antisense | 5 | 5 |
| Control, A2 antisense | 5 | 5 |
| A3 sense | 659 | 624 |
| A6 sense | 599 | 586 |

Figure 6:
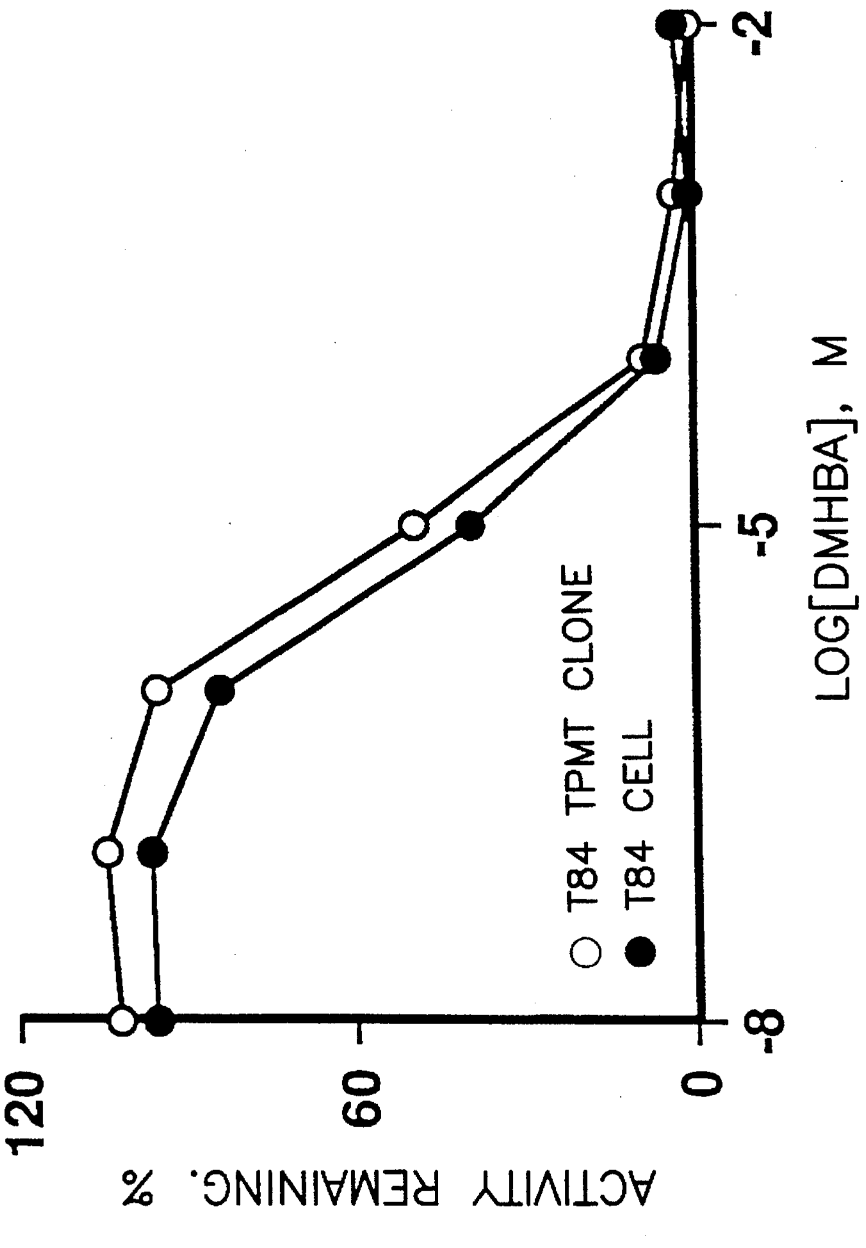
FIG. 6 is a graphical depiction of DMHBA inhibition of T84 cell TPMT activity and TPMT activity expressed in COS-1 cells transfected with T84 cell TPMT cDNA.

As shown in FIG. 6,TPMT activity expressed in the COS-1 cells transfected with the cDNA clone was inhibited by DMHBA with an $IC_{50}$ value nearly identical to that of the TPMT present in T84 cells. Finally, the response of the TPMT expressed in COS-1 cells to a panel of methyltransferase inhibitors and ions was compared with that of TPMT activity in human kidney 100,000×g supernatant, partially purified human kidney Peak I TPMT and T84 cell TPMT (Table 3).

TABLE 3

| Compound | Concentration mM | Activity Remaining, % Human Kidney 100,000 × g Supernatant | Human Kidney TPMT Peak I | T84 Cell 100,000 × g Supernatant | COS-1 Cells Transfected with T84 TPMT cDNA |
|---|---|---|---|---|---|
| Ado-Hcy | 0.1 | 5 | 5 | 5 | 5 |
| 6-MMP | 5 | 26 | 30 | 27 | 29 |
| DCMB | 1 | 95 | 95 | 99 | 95 |
| $CaCl_2$ | 1 | 96 | 97 | 95 | 96 |
| Amodiaquine | 1 | 97 | 90 | 96 | 95 |
| SKF-525A | 0.5 | 107 | 98 | 102 | 101 |

As shown by the data in Table 3, the results were nearly identical for all sources of enzyme and each activity was inhibited by the TPMT reaction products, Ado-Hcy and 6-MMP. However, the enzyme was not affected by inhibitors of other methyltransferase enzymes. The other inhibitors tested, all at effective concentrations, included DCMB and SKF-525A, inhibitors of thiol methyltransferase (TMT) (R. M. Weinshilboum et al., *Clin. Chim. Acta,* 97, 59 (1979); T. A. Glauser et al., *Drug Metab. Disposit.,* 20, 247 (1992)); amodiaquine, an inhibitor of histamine N-methyltransferase (HNMT) (A. Thithapandha et al., *Biochem. Pharmacol.,* 27, 263 (1978)); and $CaCl_2$, an inhibitor of catechol O-methyltransferase (COMT) (R. M. Weinshilboum et al., *Biochem. Pharmacol.,* 25, 573 (1976)).

Example 7

T84 Human Colon Carcinoma Cell TPMT Sequence: Comparison with Other Methyltransferases The nucleotide sequence within the open reading frame and the deduced amino acid sequence of the protein encoded by the T84 TPMT cDNA clone were compared with sequences present in the GenBank Genetics Sequence Data Bank and the EMBL Nucleotide Sequence Database. No highly homologous sequences were found. The deduced amino acid sequence of the protein encoded by the T84 TPMT cDNA clone was then compared with those of other mammalian cytosolic Ado-Met-dependent methyltransferase enzymes. The enzymes compared include rat liver guanidinoacetate methyltransferase (rGAMT, EC 2.1.1.2.); rat liver glycine methyltransferase (rGMT, EC 2.1.1.20); rat kidney histamine N-methyltransferase (rHNMT, EC 2.1.1.8); bovine pineal hydroxyindole O-methyltransferase (bHIOMT, EC 2.1.1.4); mouse testis, rat brain, and human erythrocyte protein carboxyl methyltransferase (mPCMT, rPCMT, and hPCMT, EC 2.1.1.77); rat liver and human placental catechol 0-methyltransferase (rCOMT and hCOMT, EC 2.1.1.6); rat adrenal medulla, bovine adrenal medulla and human pheochromocytoma phenylethanolamine N-methyltransferase (rPNMT, bPNMT, and hPNMT, EC 2.1.1.28) and T84 human colon carcinoma cell thiopurine methyltransferase (hTPMT, EC 2.1.1.67). The top bold value in each cell of Table 4 represents the percent identity, while the value in parentheses represents the percent similarity of sequences as determined by use of the GAP program. The stippled cells represent enzymes with greater than 75% sequence identity. Human TPMT displayed little homology with any of these enzymes, ranging from only 14.5% amino acid sequence identity when compared with rat liver guanidinoacetate methyltransferase to 24.8% identity with the sequence of human erythrocyte protein carboxyl methyltransferase.

TABLE 4

Mammalian Cytosolic Methyltransferase Enzymes
Amino Acid Sequence Comparisons

| | rGAMT | rGMT | rHNMT | bHIOMT | mPCMT | rPCMT | hPCMT |
|---|---|---|---|---|---|---|---|
| rGAMT | — | 16.9<br>(44.4) | 13.4<br>(40.2) | 20.4<br>(44.7) | 16.6<br>(36.6) | 14.6<br>(42.7) | 16.7<br>(43.4) |
| rGMT | | — | 18.0<br>(48.4) | 16.9<br>(42.7) | 23.0<br>(48.8) | 23.1<br>(50.5) | 21.4<br>(47.8) |
| rHNMT | | | — | 17.9<br>(45.9) | 20.2<br>(46.3) | 14.6<br>(39.8) | 14.3<br>(39.7) |
| bHIOMT | | | | — | 17.6<br>(47.7) | 19.1<br>(40.9) | 16.4<br>(43.6) |
| mPCMT | | | | | — | 98.7<br>(99.6) | 96.0<br>(97.8) |
| rPCMT | | | | | | — | 95.6<br>(98.2) |
| hPCMT | | | | | | | — |
| rCOMT | | | | | | | |
| hCOMT | | | | | | | |
| rPNMT | | | | | | | |
| bPNMT | | | | | | | |
| hPNMT | | | | | | | |
| hTPMT | | | | | | | |

| | rCOMT | bCOMT | rPNMT | bPNMT | hPNMT | hTPMT |
|---|---|---|---|---|---|---|
| rGAMT | 23.4<br>(43.7 | 18.4<br>(40.8) | 21.6<br>(46.8) | 19.2<br>(46.6) | 20.6<br>(48.9) | 14.5<br>(43.0) |
| rGMT | 18.3<br>(44.6) | 20.4<br>(42.3) | 21.0<br>(44.4) | 17.0<br>(39.9) | 20.2<br>(47.2) | 18.0<br>(44.3) |
| rHNMT | 17.0<br>(47.0) | 17.1<br>(46.9) | 16.3<br>(42.6) | 20.9<br>(41.1) | 17.1<br>(39.9) | 16.0<br>(43.7) |
| bHIOMT | 21.2<br>(45.7) | 16.7<br>(45.7) | 18.8<br>(45.3) | 25.3<br>(47.9) | 20.5<br>(46.8) | 17.6<br>(43.3) |
| mPCMT | 16.4<br>(45.6) | 19.4<br>(48.0) | 15.8<br>(42.3) | 16.3<br>(45.6) | 14.3<br>(42.1) | 19.6<br>(46.7) |
| rPCMT | 16.7<br>(47.1) | 19.8<br>(46.2) | 22.0<br>(45.4) | 17.1<br>(44.1) | 18.7<br>(47.8) | 19.7<br>(44.6) |
| hPCMT | 16.8<br>(44.5) | 17.1<br>(44.1) | 20.5<br>(46.3) | 19.7<br>(50.0) | 19.8<br>(46.7) | 24.8<br>(46.2) |
| rCOMT | — | 77.7<br>(87.5) | 20.9<br>(47.0) | 19.2<br>(44.0) | 17.2<br>(42.9) | 20.8<br>(51.0) |
| hCOMT | | — | 16.3<br>(38.1) | 15.8<br>(40.2) | 18.4<br>(38.8) | 22.7<br>(50.7) |
| rPNMT | | | — | 88.5<br>(91.5) | 85.9<br>(91.8) | 15.7<br>(43.9) |
| bPNMT | | | | — | 88.3<br>(92.6) | 18.5<br>(43.5) |

TABLE 4-continued

| Mammalian Cytosolic Methyltransferase Enzymes Amino Acid Sequence Comparisons | | |
|---|---|---|
| hPNMT | — | 16.7 (41.0) |
| hTPMT | | — |

The cloning of a cDNA for TPMT from a human tissue source can be used to study the molecular basis for the TPMT genetic polymorphism and can be used to develop clinically useful diagnostic tests for this polymorphism and to evaluate drugs subject to TPMT-mediated metabolism. The T84 TPMT cDNA clone can also be used to clone cDNA for TPMT from other species. Mice, like humans, exhibit a genetic polymorphism that regulates both the level of TPMT enzymatic activity and the quantity of TPMT immunoreactive protein in kidney and liver. Although R. M. Weinshilboum et al., *Mouse Genome,* 90, 446 (1992) have reported that the locus TPMT in the mouse is located on the midportion of chromosome 13, nothing is known of the molecular biology of the enzyme in mice. Cloning of a cDNA for TPMT from a human tissue will not only make it possible to study the molecular mechanism of the genetic polymorphism at the locus TPMT in the mouse, but also to initiate phylogenetic studies of the enzyme.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A mammalian cell line, the genome of which has been augmented by chromosomally integrated non-native DNA encoding mammalian thiopurine methyltransferase, wherein said DNA hybridizes with DNA complementary to DNA having SEQ ID NO:1 under the stringency conditions of hybridization in buffer containing 20% formamide, 5× Denhardt's, 6× SSC, 100 mg/ml RNA and 0.05% sodium pyrophosphate at 42° C., followed by washing at 60° C. and 1× SSC, 0.1% SDS.

2. The transgenic mammalian cell line of claim 1 wherein the mammalian cell line is a primate cell line.

3. The transgenic mammalian cell line of claims 1 or 2 wherein the mammalian TPMT is human TPMT.

4. A mammalian cell line, the genome of which has been augmented by chromosomally integrated non-native DNA encoding human thiopurine methyl transferase having an amino acid sequence which is SEQ ID NO:2.

5. The mammalian cell line of claim 4, wherein the non-native DNA has the sequence consisting of SEQ ID NO:1.

6. An isolated and purified DNA encoding human thiopurine methyl transferase that hybridizes to DNA complementary to DNA having SEQ ID NO:1 under the stringency conditions of hybridization in buffer containing 20% formamide, 5× Denhardt's, 6× SSC, 100 mg/ml RNA and 0.05% sodium pyrophosphate at 42° C., followed by washing at 60° C. and 1× SSC, 0.1% SDS.

7. An isolated and purified DNA encoding only the human thiopurine methyl transferase having an amino acid sequence which is SEQ ID NO:2.

8. The DNA of claim 7 which has SEQ ID NO:1.

9. An isolated and purified DNA which functions to express human thiopurine methyltransferase when introduced into a mammalian cell, wherein said DNA is not native to said cell and comprises the DNA of claims 6, 7 or 8, operably linked to a promoter functional in said mammalian cell.

* * * * *

UNITED STATES PATENT AND TRADEMARK OFFICE

CERTIFICATE OF CORRECTION

PATENT NO. : 5,470,737

DATED : November 28, 1995

INVENTOR(S) : Richard M. Weinshilboum et al.

It is certified that error appears in the above-indentified patent and that said Letters Patent is hereby corrected as shown below:

Column 1, Line 59, please delete "polypspride" and insert --polypeptide-- therefor.

Column 2, Line 13, please delete "^" and insert --Δ-- therefor.

Column 3, Line 4, please delete "eDNA " and insert --cDNA-- therefor.

Signed and Sealed this

Thirtieth Day of July, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 2743 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: T84 human colon carcinoma cell TPMT cDNA clone ( i x ) FEATURE:
( A ) NAME/KEY: CDS
( B ) LOCATION: 66..801

( x i ) SEQUENCE DESCRIPTION: SEQ ID NO:1:

```
CGGCAACCAG CTGTAAGCGA GGCACGGAAG ACATATGCTT GTGAGACAAA GGTGTCTCTG       60

AAACT ATG GAT GGT ACA AGA ACT TCA CTT GAC ATT GAA GAG TAC TCG          107
      Met Asp Gly Thr Arg Thr Ser Leu Asp Ile Glu Glu Tyr Ser
      1               5                   10

GAT ACT GAG GTA CAG AAA AAC CAA GTA CTA ACT CTG GAA GAA TGG CAA      155
Asp Thr Glu Val Gln Lys Asn Gln Val Leu Thr Leu Glu Glu Trp Gln
15                  20                  25                  30

GAC AAG TGG GTG AAC GGC AAG ACT GCT TTT CAT CAG GAA CAA GGA CAT      203
Asp Lys Trp Val Asn Gly Lys Thr Ala Phe His Gln Glu Gln Gly His
                35                  40                  45

CAG CTA TTA AAG AAG CAT TTA GAT ACT TTC CTT AAA GGC AAG AGT GGA      251
Gln Leu Leu Lys Lys His Leu Asp Thr Phe Leu Lys Gly Lys Ser Gly
            50                  55                  60

CTG AGG GTA TTT TTT CCT CTT TGC GGA AAA GCG GTT GAG ATG AAA TGG      299
Leu Arg Val Phe Phe Pro Leu Cys Gly Lys Ala Val Glu Met Lys Trp
```

-continued 65 70 75

TTT GCA GAC CGG GGA CAC AGT GTA GTT GGT GTG GAA ATC AGT GAA CTT 347
Phe Ala Asp Arg Gly His Ser Val Val Gly Val Glu Ile Ser Glu Leu
80 85 90

GGG ATA CAA GAA TTT TTT ACA GAG CAG AAT CTT TCT TAC TCA GAA GAA 395
Gly Ile Gln Glu Phe Phe Thr Glu Gln Asn Leu Ser Tyr Ser Glu Glu
95 100 105 110

CCA ATC ACC GAA ATT CCT GGA ACC AAA GTA TTT AAG AGT TCT TCG GGG 443
Pro Ile Thr Glu Ile Pro Gly Thr Lys Val Phe Lys Ser Ser Ser Gly
115 120 125

AAC ATT TCA TTG TAC TGT TGC AGT ATT TTT GAT CTT CCC AGG ACA AAT 491
Asn Ile Ser Leu Tyr Cys Cys Ser Ile Phe Asp Leu Pro Arg Thr Asn
130 135 140

ATT GGC AAA TTT GAC ATG ATT TGG GAT AGA GGA GCA TTA GTT GCC ATT 539
Ile Gly Lys Phe Asp Met Ile Trp Asp Arg Gly Ala Leu Val Ala Ile
145 150 155

AAT CCA GGT GAT CGC AAA TGC TAT GCA GAT ACA ATG TTT TCC CTC CTG 587
Asn Pro Gly Asp Arg Lys Cys Tyr Ala Asp Thr Met Phe Ser Leu Leu
160 165 170

GGA AAG AAG TTT CAG TAT CTC CTG TGT GTT CTT TCT TAT GAT CCA ACT 635
Gly Lys Lys Phe Gln Tyr Leu Leu Cys Val Leu Ser Tyr Asp Pro Thr
175 180 185 190

AAA CAT CCA GGT CCA CCA TTT TAT GTT CCA CAT GCT GAA ATT GAA AGG 683
Lys His Pro Gly Pro Pro Phe Tyr Val Pro His Ala Glu Ile Glu Arg
195 200 205

TTG TTT GGT AAA ATA TGC AAT ATA CGT TGT CTT GAG AAG GTT GAT GCT 731
Leu Phe Gly Lys Ile Cys Asn Ile Arg Cys Leu Glu Lys Val Asp Ala
210 215 220

TTT GAA GAA CGA CAT AAA AGT TGG GGA ATT GAC TGT CTT TTT GAA AAG 779
Phe Glu Glu Arg His Lys Ser Trp Gly Ile Asp Cys Leu Phe Glu Lys
225 230 235

TTA TAT CTA CTT ACA GAA AAG T AAATGAGACA TAGATAAAAT AAAATCACAC 831
Leu Tyr Leu Leu Thr Glu Lys
240 245

TGACATGTTT TTGAGGAATT GAAAATTATG CTAAAGCCTG AAAATGTAAT GGATGAATTT 891

TTAAAATTGT TTATAAATCA TATGATAGAT CTTTACTAAA AATGGCTTTT TAGTAAAGCC 951

ATTTACTTTT TCTAAAAAAG TTTTAGAAGA AAAAGATGTA ACTAAACTTT TAAAGTAGCT 1011

CCTTTGGAGA GGAGATTATG ATGTGAAAGA TTATGCCTAT GTGTCTTGCA GATTGCAAGA 1071

TATTTTACCA ATCAGCATGT GTTACCTGTA CAATTAAAAA AATATTTCAA AATGCAATGC 1131

ATATTAAATA TAATACACAC AGAAAAACTG GCATTTATTT TGTTTTATTT TTTTGAGATG 1191

GAGTTTCGTT CTTGTTGCCC AACCTGGAGT GCAGTGGTGC GGTCTCGGCT CACTGCAACC 1251

TCTGCCTCCC GGGTTCGGGT GGTTCTCCTG CCTCGGCCTC CTGAGTGGCT GGGATTGCAG 1311

GTGTGCGCCA CCACGCCCGG CTAGTTTTTT GTGTTTTTAG TGGAGACGGG GTTTCACCAT 1371

GTTGGTCAGG CTGATCTCGA GCTCCTGACC TCAGGTGATC TACCCACCTC GGCCTCCCAA 1431

AGTGCTGGGA TTACAGGCGT GAGCCACTGC ACCTGGCCTG ACATTCTTTA TGAAATTTAG 1491

AATTGTTGAA GAACTATAAC ATTTCAGTAG GGTTCAAGGT GGTCCCAAAA GTTATATAAA 1551

AGATTAGTTT TTACTATAAA CCCTTGTCTT TTACTCAGAT CCTAGCATCC CTTTTCACAT 1611

GGTTTCTCCA TGTATATAAC AGAATCAAGA AACAAATTTT AATTAAACAA TCTGTAACAG 1671

AATCAAGAAA CAAATACATT TTAATTAAAC AATCTATATG GAACAAACAT TCCCAAATTC 1731

TAAGAATAAA TTTTTCTTTA AGTTTTCTCT GAGTTTGGCA ATTGTTGTTT TTTATAATTT 1791

AATCTGTTTA AATCATCAGG TCTTATAAAA TATAATGTAC TTAGAGCTGG ATTCATGGCT 1851

-continued

| | | | | | |
|---|---|---|---|---|---|
| GTTTATTATG | AAAGGTTAGA | TTTCTCAGTT | CTTCTTTAAC | CACATTTTGT | TATATCAGAC | 1911 |
| AGTCCTCTAT | AACTCTGTAC | TACCCAACAA | CTAAATGGTT | TAGATTGTTT | AGCTCATGTT | 1971 |
| AATAGGATGG | TTGTGTATTA | TAAAAAACGA | GTTACGTGTG | TGTGTGCACG | CATGCACGCA | 2031 |
| CATGTGCTGG | CTTAAAGGTT | GTTAATGCAA | GGTTTGGGGT | CCCCTTTAAC | ACTGGTGAAA | 2091 |
| GCTACGGTAC | TCTCCCCAGA | GATATGTCTT | GTCAGCCTCT | CTAGTTCCCC | TTGGCCTGCA | 2151 |
| TGTACAAACT | TCTACCCTAG | AAGCTCTCTG | CCATCGATGT | ATTCTAATAG | ATTTGTAAGG | 2211 |
| CTATTAATTT | GAAGCAACTC | CTTGCTCACA | GTGATTCTTG | CTTCTCTGAG | ACCTGCTCCC | 2271 |
| AGTCGATACT | GTGGGCTTCA | GAAGCCATGA | CTCCCCAACT | CTGCCTGTAT | CACCGGTTGA | 2331 |
| ATGGACAACT | AACCCGAGCT | GGACCAACAC | AATTCTCTCC | AGAGACTTTT | GATTTTACTT | 2391 |
| TTATGTAGAG | ACAGGGTCTC | ACTTTGTTGC | CCACGCTGAT | GTTGAACTTG | ACGTGAGGCC | 2451 |
| TCAAGCAGTC | CTCCTGTCTT | GGCCACCCAA | AGTGCTAGGA | TTACAGGTAT | GAGCCATTGC | 2511 |
| GCTGGCCCTC | TTCATAGGCT | TTTGGACTTG | GGAATAGAAA | AGCAACCCCG | TCTCTACTGA | 2571 |
| AAGTGCAGAA | GGATTGGCCG | GGCGTGGTGG | CGCGTGCCTG | TGGTCCCAGC | TGCTTGGGGG | 2631 |
| GCTGAGGCGG | GAGAATCACT | TGGACCTGGG | GGGCGGAGGT | TGCAGTGAGC | TGAGATCGTG | 2691 |
| CCACTGCACG | CCAGCCTGGG | CAACAGAGCA | AGACTCTGTC | TCAAAAGAAA | GA | 2743 |

( 2 ) INFORMATION FOR SEQ ID NO:2:

( i ) SEQUENCE CHARACTERISTICS:
  ( A ) LENGTH: 245 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Asp Gly Thr Arg Thr Ser Leu Asp Ile Glu Glu Tyr Ser Asp Thr
 1               5                  10                  15

Glu Val Gln Lys Asn Gln Val Leu Thr Leu Glu Glu Trp Gln Asp Lys
            20                  25                  30

Trp Val Asn Gly Lys Thr Ala Phe His Gln Glu Gln Gly His Gln Leu
        35                  40                  45

Leu Lys Lys His Leu Asp Thr Phe Leu Lys Gly Lys Ser Gly Leu Arg
    50                  55                  60

Val Phe Phe Pro Leu Cys Gly Lys Ala Val Glu Met Lys Trp Phe Ala
65                  70                  75                  80

Asp Arg Gly His Ser Val Val Gly Val Glu Ile Ser Glu Leu Gly Ile
                85                  90                  95

Gln Glu Phe Phe Thr Glu Gln Asn Leu Ser Tyr Ser Glu Glu Pro Ile
            100                 105                 110

Thr Glu Ile Pro Gly Thr Lys Val Phe Lys Ser Ser Ser Gly Asn Ile
        115                 120                 125

Ser Leu Tyr Cys Cys Ser Ile Phe Asp Leu Pro Arg Thr Asn Ile Gly
    130                 135                 140

Lys Phe Asp Met Ile Trp Asp Arg Gly Ala Leu Val Ala Ile Asn Pro
145                 150                 155                 160

Gly Asp Arg Lys Cys Tyr Ala Asp Thr Met Phe Ser Leu Leu Gly Lys
                165                 170                 175

Lys Phe Gln Tyr Leu Leu Cys Val Leu Ser Tyr Asp Pro Thr Lys His
            180                 185                 190
```

-continued

| | | | | | | | | | | | | | | | |
|---|---|---|---|---|---|---|---|---|---|---|---|---|---|---|---|
| Pro | Gly | Pro | Pro | Phe | Tyr | Val | Pro | His | Ala | Glu | Ile | Glu | Arg | Leu | Phe |
| | | 195 | | | | | 200 | | | | | 205 | | | |
| Gly | Lys | Ile | Cys | Asn | Ile | Arg | Cys | Leu | Glu | Lys | Val | Asp | Ala | Phe | Glu |
| | 210 | | | | | 215 | | | | | 220 | | | | |
| Glu | Arg | His | Lys | Ser | Trp | Gly | Ile | Asp | Cys | Leu | Phe | Glu | Lys | Leu | Tyr |
| 225 | | | | | 230 | | | | | 235 | | | | | 240 |
| Leu | Leu | Thr | Glu | Lys | | | | | | | | | | | |
| | | | | 245 | | | | | | | | | | | |

( 2 ) INFORMATION FOR SEQ ID NO:3:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( B ) CLONE: Human kidney TPMT Papain digest ( x i ) SEQUENCE DESCRIPTION: SEQ ID NO:3:

| | | | | | | | | | | | | | | | |
|---|---|---|---|---|---|---|---|---|---|---|---|---|---|---|---|
| Val | Glu | Ile | Ser | Glu | Leu | Gly | Ile | Gln | Glu | Phe | Phe | Thr | Glu | Gln | Asn |
| 1 | | | | 5 | | | | | 10 | | | | | 15 | |
| Leu | | | | | | | | | | | | | | | |

( 2 ) INFORMATION FOR SEQ ID NO:4:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( B ) CLONE: Human kidney TPMT V8 protease digest ( x i ) SEQUENCE DESCRIPTION: SEQ ID NO:4:

| | | | | | | | | | | | | | | |
|---|---|---|---|---|---|---|---|---|---|---|---|---|---|---|
| Phe | Phe | Thr | Glu | Gln | Asn | Leu | Ser | Tyr | Xaa | Glu | Glu | Pro | Ile | Thr |
| 1 | | | | 5 | | | | | 10 | | | | | 15 |

( 2 ) INFORMATION FOR SEQ ID NO:5:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

| | | | | | | | | | | | |
|---|---|---|---|---|---|---|---|---|---|---|---|
| Phe | Ser | Leu | Leu | Xaa | Lys | Lys | Phe | Xaa | Tyr | Leu | Leu |
| 1 | | | | 5 | | | | | 10 | | |

( 2 ) INFORMATION FOR SEQ ID NO:6:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide -continued ( v i i ) IMMEDIATE SOURCE:
( B ) CLONE: 5 kDa Cyanogen bromide subunit of human kidney TPMT ( x i ) SEQUENCE DESCRIPTION: SEQ ID NO:6:

```
Asp Gly Thr Arg Thr Ser Leu Asp Ile Glu Glu Tyr
1               5                   10
```

( 2 ) INFORMATION FOR SEQ ID NO:7:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

```
Ile Gln Glu Phe Phe Thr Glu Gln Asn Leu Ser Tyr Xaa Glu Glu Pro
1               5                   10                  15

Ile Thr
```

( 2 ) INFORMATION FOR SEQ ID NO:8:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

```
GTCTCTAGAA THCARGARTT YTTYAC                                          26
```

( 2 ) INFORMATION FOR SEQ ID NO:9:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

```
GTCGAATTCG THATNGGYTC YTC                                             23
```

( 2 ) INFORMATION FOR SEQ ID NO:10:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

```
GTCTCTAGAA TTCAGGAATT TTTTACAGAG CAGAATCTTT CTTACTCAGA GGAACCCATC     60

ACGAATTCGA C                                                          71
```

( 2 ) INFORMATION FOR SEQ ID NO:11:

( i ) SEQUENCE CHARACTERISTICS:
( A ) LENGTH: 53 base pairs

-continued ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

ATTCAGGAAT TTTTTACAGA GCAGAATCTT TCTTACTCAG AGGAACCCAT CAC 53

( 2 ) INFORMATION FOR SEQ ID NO:12:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

ACAGAGCAGA ATCTTTC 17

( 2 ) INFORMATION FOR SEQ ID NO:13:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

GAATTCAAAC CATGGATGGT ACAAGAACT 29

( 2 ) INFORMATION FOR SEQ ID NO:14:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:14:

GAATTCTCAT TTACTTTTCT GTAAGTAGAT 30

( 2 ) INFORMATION FOR SEQ ID NO:15:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( i x ) FEATURE:
( D ) OTHER INFORMATION: /note="The Xaa in location 3 can be an Asp or Glu"

( x i ) SEQUENCE DESCRIPTION: SEQ ID NO:15:

Xaa Xaa Xaa Xaa Gly Xaa Gly Xaa Gly Xaa Xaa Xaa Xaa Xaa Xaa Xaa
1 5 10 15

Xaa ( 2 ) INFORMATION FOR SEQ ID NO:16:

-continued ( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( D ) OTHER INFORMATION: /note="The Xaa in location 2 can be an Asp or Glu"

( x i ) SEQUENCE DESCRIPTION: SEQ ID NO:16:

```
Leu Xaa Xaa Gly Xaa Gly Xaa Gly
1               5
```

( 2 ) INFORMATION FOR SEQ ID NO:17:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( D ) OTHER INFORMATION: /note="The Xaa in location 2 can be an Arg or Lys"

( x i ) SEQUENCE DESCRIPTION: SEQ ID NO:17:

```
Leu Xaa Pro Gly Gly Xaa Leu
    1               5
```

( 2 ) INFORMATION FOR SEQ ID NO:18:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: cDNA ( x i ) SEQUENCE DESCRIPTION: SEQ ID NO:18:

```
Glu Glu Pro Ile Thr
1               5
```